United States Patent
Combette et al.

(10) Patent No.: US 10,098,925 B2
(45) Date of Patent: Oct. 16, 2018

(54) PROTEIN SLURP-1 FOR USE IN THE TREATMENT OF OCULAR DISEASES

(71) Applicant: Brightpulse Holding Ltd., Limassol (CY)

(72) Inventors: Jean-Marc Combette, Saint-cergues (FR); Catherine Deloche, Geneva (CH); Claire Abadie, Annecy (FR); Sebastien Mouz, Villaz (FR); Julien Perino, Evian les Bains (FR)

(73) Assignee: Brightpulse Holding Ltd., Limassol (CY)

( * ) Notice: Subject to any disclaimer, the term of this patent is extended or adjusted under 35 U.S.C. 154(b) by 0 days.

(21) Appl. No.: 14/650,277

(22) PCT Filed: Dec. 9, 2013

(86) PCT No.: PCT/EP2013/075981
§ 371 (c)(1),
(2) Date: Jun. 5, 2015

(87) PCT Pub. No.: WO2014/087022
PCT Pub. Date: Jun. 12, 2014

(65) Prior Publication Data
US 2015/0320831 A1 Nov. 12, 2015

(30) Foreign Application Priority Data
Dec. 7, 2012 (EP) .................................. 12196007

(51) Int. Cl.
*A61K 38/17* (2006.01)
*A61K 47/36* (2006.01)
*A61K 9/00* (2006.01)

(52) U.S. Cl.
CPC .......... *A61K 38/177* (2013.01); *A61K 9/0048* (2013.01); *A61K 38/1709* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 7,135,454 | B2 * | 11/2006 | Chimienti | A61K 38/177 514/17.5 |
| 2013/0012456 | A1 * | 1/2013 | Walz | A61K 47/48169 514/21.4 |
| 2013/0122066 | A1 * | 5/2013 | Ploeger | A61L 15/44 424/400 |
| 2014/0127163 | A1 * | 5/2014 | Swamynathan | A61K 38/177 424/93.2 |
| 2015/0290172 | A1 * | 10/2015 | Kimura | A61K 31/415 548/376.1 |
| 2015/0320831 | A1 * | 11/2015 | Combette | A61K 38/1709 514/20.8 |

FOREIGN PATENT DOCUMENTS

| | | | |
|---|---|---|---|
| WO | 94/14959 | A1 | 7/1994 |
| WO | 2004/091646 | A2 | 10/2004 |
| WO | WO 2004091646 | * | 10/2004 |
| WO | 2010/138379 | A2 | 12/2010 |

OTHER PUBLICATIONS

Alexander et al. ("Novel cholinergic peptides SLURP-1 and -2 regulate epithelialization of cutaneous and oral wounds", Wound Repair and Regeneration, vol. 20, No. 1, Jan. 1, 2012, pp. 103-113).*
Elder et al.: "Progression of disease in ocular cicatricial pemphigoid", British Journal of Opthalmology, vol. 80, No. 4, 1996, pp. 292-296.*
https://en.wikipedia.org/wiki/Cicatrization.*
Adermann et al., "Structural and phylogenetic characterization of human SLURP-1, the first secreted mammalian member of the Ly-6/uPAR protein superfamily," *Protein Science 8*: 810-819, 1999.
Arredondo et al., "SLURP-2: A Novel Cholinergic Signaling Peptide in Human Mucocutaneous Epithelium," *Journal of Cellular Physiology 208*: 238-245, 2006.
Chernyaysky et al., "Coupling of Ionic Events to Protein Kinase Signaling Cascades upon Activation of α7 Nicotinic Receptor," *The Journal of Biological Chemistry 284*(33): 22140-22148, Aug. 14, 2009.
Chernyaysky et al., "Novel cholinergic peptides SLURP-1 and -2 regulate epithelialization of cutaneous and oral wounds," *Wound Rep Reg 20*: 103-113, 2012.
Chimienti et al., "Identification of SLURP-1 as an epidermal neuromodulator explains the clinical phenotype of Mal de Meleda," *Human Molecular Genetics 12*(22): 3017-3024, 2003.
Grando, "Cholinergic control of epidermal cohesion," *Experimental Dermatology 15*: 265-282, 2006.
Grando et al., "Adrenergic and Cholinergic Control in the Biology of Epidermis: Physiological and Clinical Significance," *Journal of Investigative Dermatology 126*: 1948-1965, 2006.
Hattori et al., "Effects of all-trans retinoic acid nanoparticles on corneal epithelial wound healing," *Graefes Arch Clin Exp Ophthalmol*, DOI 10.1007/s00417-011-1849-8, 2011, 7 pages.
Mastrangeli et al., "ARS Component B: structural characterization, tissue expression and regulation of the gene and protein (SLURP-1) associated with Mal de Meleda," *Eur J Dermatol 13*(6): 560-570, Nov.-Dec. 2003.
Chernyavsky et al., "Novel cholinergic peptides SLURP-1 and -2 regulate epithelialization of cutaneous and oral wounds," *Wound Rep Reg 20*:103-113, 2012.
Elder et al., "Progression of disease in ocular cicatricial pemphigoid," *British Journal of Ophthalmology 80*:292-296, 1996.
Swamynathan et al., "Klf4 Regulates the Expression of Slurp1, Which Functions as an Immunomodulatory Peptide in the Mouse Cornea," *Invest Ophthalmol Vis Sci 53*(13):8433-8446, 2012.

* cited by examiner

Primary Examiner — Maury A Audet
(74) Attorney, Agent, or Firm — Seed IP Law Group LLP

(57) ABSTRACT

The present invention relates to a protein comprising SEQ ID NO:1 (mature form of SLURP-1) and to a composition comprising the same for use in inducing or accelerating cicatrization, and/or in preventing infection in the eye of a subject.

14 Claims, 5 Drawing Sheets
Specification includes a Sequence Listing.

CLUSTAL 2.1 multiple sequence alignment

```
Full      MASRWAVQLLLVAAWSMGCGEALKCYTCKEPMTSASCRTITRCKPEDTACMTILVTVEAE 60
Mature    ------------------------LKCYTCKEPMTSASCRTITRCKPEDTACMTILVTVEAE 33
                                  ************************************

Full      YFFNQSPVVTRSCSSSCVATDPDSIGAAHLIFCCFRDLCNSEL 103  SEQ ID NO:2
Mature    YFFNQSPVVTRSCSSSCVATDPDSIGAAHLIFCCFRDLCNSEL  81  SEQ ID NO:1
          ******************************************
```

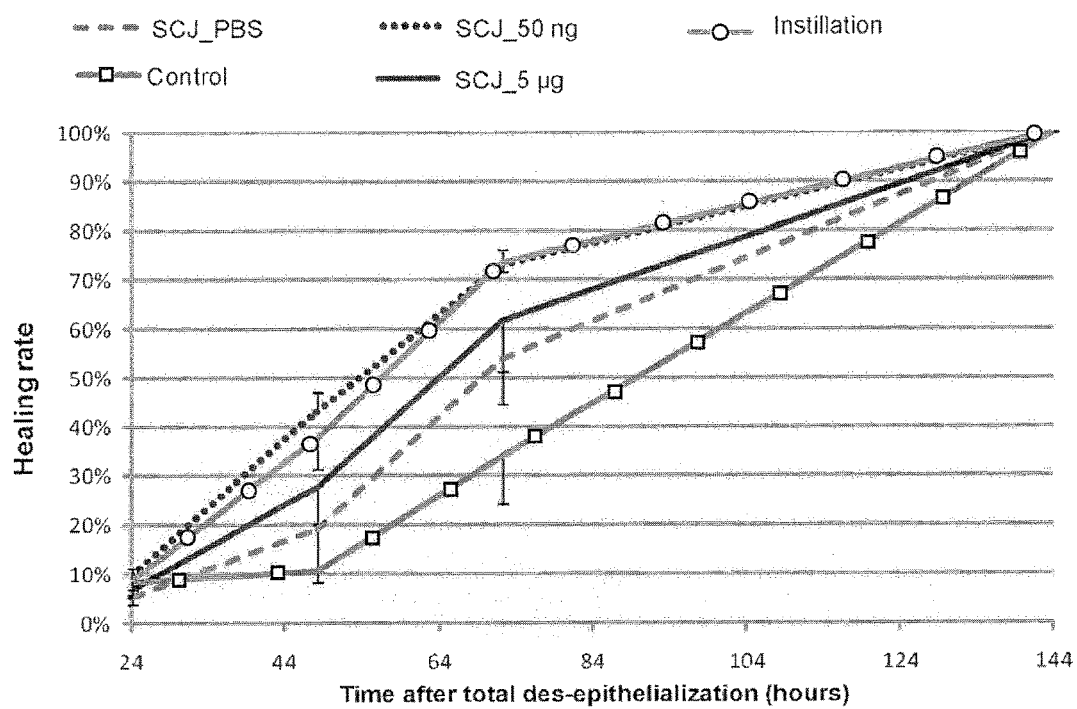
FIG. 3a
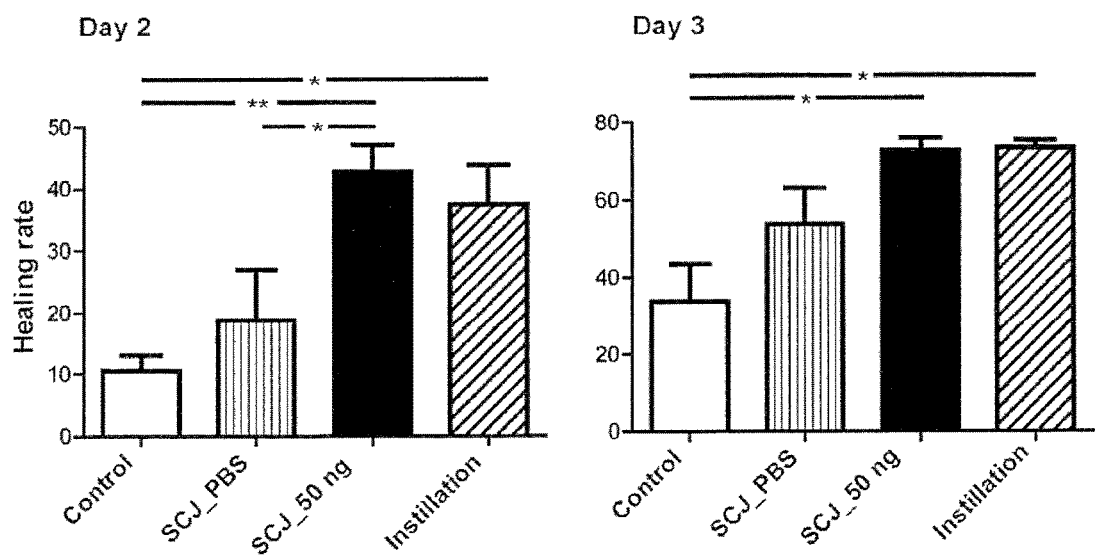
FIG. 3b
FIG. 3c

100% open wound, 0% wound closure

10 µg/ml SLURP-1

Control (No treatment)

SEQUENCE LISTING

```
<160> NUMBER OF SEQ ID NOS: 3

<210> SEQ ID NO 1
<211> LENGTH: 81
<212> TYPE: PRT
<213> ORGANISM: Homo sapiens
<220> FEATURE:
<221> NAME/KEY: SOURCE
<222> LOCATION: 1..81
<223> OTHER INFORMATION: protein Homo sapiens

<400> SEQUENCE: 1

Leu Lys Cys Tyr Thr Cys Lys Glu Pro Met Thr Ser Ala Ser Cys Arg
1               5                   10                  15

Thr Ile Thr Arg Cys Lys Pro Glu Asp Thr Ala Cys Met Thr Thr Leu
            20                  25                  30
```

Val Thr Val Glu Ala Glu Tyr Pro Phe Asn Gln Ser Pro Val Val Thr
            35                  40                  45

Arg Ser Cys Ser Ser Cys Val Ala Thr Asp Pro Asp Ser Ile Gly
        50                  55                  60

Ala Ala His Leu Ile Phe Cys Cys Phe Arg Asp Leu Cys Asn Ser Glu
65                  70                  75                  80

Leu

<210> SEQ ID NO 2
<211> LENGTH: 103
<212> TYPE: PRT
<213> ORGANISM: Homo sapiens
<220> FEATURE:
<221> NAME/KEY: SOURCE
<222> LOCATION: 1..103
<223> OTHER INFORMATION: protein Homo sapiens

<400> SEQUENCE: 2

Met Ala Ser Arg Trp Ala Val Gln Leu Leu Val Ala Ala Trp Ser
1               5                   10                  15

Met Gly Cys Gly Glu Ala Leu Lys Cys Tyr Thr Cys Lys Glu Pro Met
                20                  25                  30

Thr Ser Ala Ser Cys Arg Thr Ile Thr Arg Cys Lys Pro Glu Asp Thr
            35                  40                  45

Ala Cys Met Thr Thr Leu Val Thr Val Glu Ala Glu Tyr Pro Phe Asn
        50                  55                  60

Gln Ser Pro Val Val Thr Arg Ser Cys Ser Ser Cys Val Ala Thr
65                  70                  75                  80

Asp Pro Asp Ser Ile Gly Ala Ala His Leu Ile Phe Cys Cys Phe Arg
                85                  90                  95

Asp Leu Cys Asn Ser Glu Leu
            100

<210> SEQ ID NO 3
<211> LENGTH: 8
<212> TYPE: PRT
<213> ORGANISM: Artificial Sequence
<220> FEATURE:
<223> OTHER INFORMATION: C terminal consensus sequence
<220> FEATURE:
<221> NAME/KEY: VARIANT
<222> LOCATION: (1)...(8)
<223> OTHER INFORMATION: Xaa = Any Amino Acid

<400> SEQUENCE: 3

Cys Cys Xaa Xaa Xaa Xaa Cys Asn
1               5

PROTEIN SLURP-1 FOR USE IN THE TREATMENT OF OCULAR DISEASES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 180048_401USPC_SEQUENCE_LISTINGtxt. The text file is 2.3 KB, was created on Jun. 4, 2015, and is being submitted electronically via EFS-Web.

The present invention relates to a protein comprising SEQ ID NO:1 and a composition comprising the same for use in inducing or accelerating cicatrisation in the eye of a subject and/or in preventing infection in the eye of a subject.

STATE OF THE ART

Ocular, in particular corneal and conjunctival, lesions are one of the most diagnosed conditions in patients consulting their physician, and one of the major causes of sight loss. These lesions may be of various origins but are mainly due to allergy, infections (bacterial, viral and fungal), dry eye syndrome, surgery and other traumatisms. These lesions are harmful and very painful. Symptoms of these lesions may be dryness, burning and a sandy-gritty eye irritation. Symptoms may also be described as itchy, scratchy, stingy or tired eyes. Other symptoms are ocular pain, redness, a pulling sensation, and pressure behind the eye. The damage to the eye surface increases discomfort and sensitivity to bright light.

Ocular surface lesions need to be treated and healed up very rapidly to avoid worsening of the situation and complications such as ulceration, which may lead to loss of visual acuity and blindness in the most severe cases. For the treatment of lesions due to dry eye syndrome, many lubricating solutions and hydrating hydrogels exist. However, these products only relieve the symptoms but do not accelerate the healing process of the lesions.

For deeper lesions, there are some vitamin A solutions and compositions enhancing mucin secretion, which may help in healing but have a limited efficiency.

Although there are some chemical compounds and biological molecules which have been found to be implicated in wound healing in other tissues, the choice for the specific application to the eye is still very narrow and no effective molecules are currently available.

Human component B (hereinafter referred to as SLURP-1) is a member of the Ly-6/uPAR superfamily as demonstrated via amino acid sequence comparison. This superfamily contains a C-terminal consensus sequence CCXXXXCN (SEQ ID NO: 3) and different numbers of Ly-6/uPAR domain repeats. The whole sequence contains multiple cysteine residues (from eight to ten)[1-3] leading to protein specific disulfide bonds.

The Ly-6/uPAR superfamily can be divided in two subfamilies depending on the presence of GPI anchoring signal sequences[4].

SLURP-1 belongs to the first subfamily of the Ly-6/uPAR superfamily and has no GPI-anchoring signal sequence. SLURP-2 is also a member of the same subfamily[4,5]. Patients with Mal de Meleda (MdM) are often associated with a mutation in SLURP-1 and the MdM gene is located in a cluster of Ly-6 genes on chromosome 8q24.3[6-9].

The second subfamily comprises proteins with a GPI anchoring signal and includes several proteins: retinoic acid-induced gene E (RIG-E), E48 antigen (human Ly-6D), Ly6H, prostate stem cell antigen (PSCA), CD59 or protectin, Lynx1 and uPAR (urokinase receptor)[10-15].

SLURP-1 is described in WO 94/14959. Briefly, the protein was first discovered and purified from a dialyzed urine concentrate after treatment with an adsorbing agent and a specific purification process. It is an 81 amino acid (SEQ ID NO:1) protein in its mature form (103 amino acid—SEQ ID NO:2—with the N-terminal signal peptide) which has a molecular weight around 8.9 kD. Its sequence is located on the long arm of human chromosome 8 as many of the Ly6/uPAR superfamily members, confirming a potential co-evolution after chromosomal duplication events.[4]

SLURP-1 exists in two different forms depending on the presence of a sulfate group on the tyrosine at position 39: type 1 is sulfated while type 2 is not. SLURP-1 is detected in multiple organs and fluids like blood and urine. It is mainly produced by keratinocytes and epithelial cells, hence having a main epithelial tissue distribution[19-24].

Moreover, phylogenetic analysis demonstrated close relationship between SLURP-1 and Ly-6/uPAR superfamily members but also with snake neurotoxins[4]. Snake neurotoxins show an inhibitory effect on acetylcholine receptors, hence inhibiting ion exchange between cells and extracellular media and subsequently preventing cell signalling[16,17]. The important sequence homology between snake neurotoxins and SLURP-1 is emphasized by the three-dimensional structure similarity: SLURP-1 is likely to have a "three-finger" appearance, a specific feature of snake proteins[18,19]. The resemblance of both proteins and the inhibitory activity of snake neurotoxins pointed out that SLURP-1 might be used to bind and interact with ion channels like nicotinic acetylcholine receptors.

Activation of nAChRs in non-neuronal cells could modify gene expression of proteins implicated in processes such as cell cycle regulation, apoptosis, cell-cell and cell-substrate interaction. The main studied homomeric receptor is composed of α7 subunits; the activation of this specific receptor is transduced by different initial signals however leading to a common end point. Transduced signals simultaneously involve ionic events and protein kinase signaling. Chernyaysky et al concluded that this twin activation (ionic events and protein kinase signaling) could lead to gene expression and simultaneous changes in cell morphology (and subsequent locomotion of keratinocytes)[20]. The simultaneous and complementary signaling was clearly demonstrated by inhibiting either ionic or protein signaling which led to partial inhibition while inhibiting both mechanisms led to complete inhibition of their effects.

The interaction between SLURP-1 and nicotinic receptors was confirmed in different publications and in the presence of acetylcholine, an agonist activity (contrary to snake neurotoxins) was discovered on human keratinocytes while using SLURP-1[21]. This interaction regulates cell functions through cholinergic pathways and probably leads to epithelial cell adhesion, motility and wound healing[22,23], however discordant results were obtained by a team leading to conclude that SLURP-1 was slowing down healing process while SLURP-2 was accelerating it.[26] These results were yet to be compared with a third experiment from the same group stating that the combination of SLURP-1 and SLURP-2 leads to an additive positive effect on the skin healing process when compared to either SLURP-1 inhibiting or SLURP-2 accelerating activities on their own.

Further research is needed to ascertain whether SLURP-1 or SLURP-2 are useful for wound healing in general.

Moreover, the need is strongly felt in the field of ophthalmics to develop medicaments and related compositions to promote healing following ocular disease with high efficiency, no counter-effects and recovery of complete corneal transparency.

It is an object of the present invention to provide biological molecules and/or compositions for use in the treatment of ocular disease, in particular in inducing or accelerating cicatrisation, reducing inflammation, and preventing infection in the eye of a subject.

The above said object is achieved by the present invention, as it relates to a protein as defined in claim 1.

Unless defined otherwise, all technical and scientific terms used herein have the same meaning as commonly understood by one of ordinary skill in the art to which this invention pertains. Although many methods and materials similar or equivalent to those described herein may be used in the practice or testing of the present invention, preferred methods and materials are described below. Unless mentioned otherwise, the techniques described herein for use with the invention are standard methodologies well known to persons of ordinary skill in the art.

BRIEF DESCRIPTION OF THE DRAWINGS

FIG. 3A is a graph showing the time course of corneal wound healing after total des-epithelialization in control and SLURP-1 treated groups. Calculated healing rate means±SEM.

FIG. 3B shows a graph of the healing rate on day two after total des-epithelialization in control and SLURP-1 treated groups (subconjunctival administration with 50 ng of SLURP and instillation).

FIG. 3C shows a graph of the healing rate on day three after total des-epithelialization in control and SLURP-1 treated groups (subconjunctival administration with 50 ng of SLURP and instillation).

DETAILED DESCRIPTION OF THE INVENTION

Figures 1, 2:
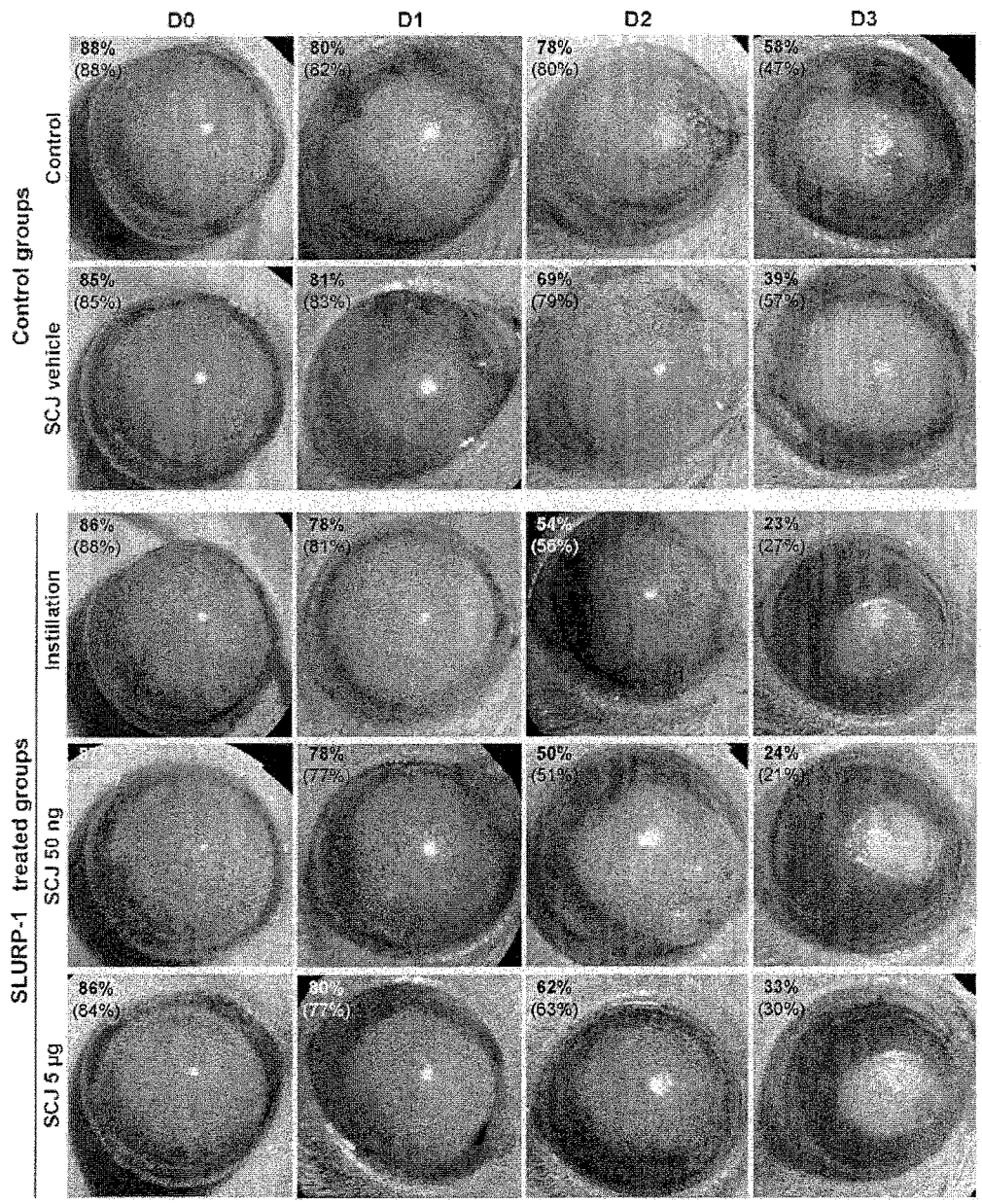
FIG. 1 shows a sequence comparison between the amino acid sequence of the full-length, SEQ ID NO:2, and mature SLURP-1 protein, SEQ ID NO:1, (respectively amino acids 1-103 and amino acids 23-103)
FIG. 2 shows images of fluorescein staining of corneal epithelial wounds at the indicated time points after total alcohol-induced des-epithelialization in control and SLURP-1 treated groups. The control groups include one group that received no treatment (control) and one group that was treated with subconjunctival injection of the vehicle (PBS) (SCJ vehicle). Bold percentages indicate the group means of the corneal wound surface, and percentages in brackets indicate the value of the representative cornea for the considered group.

According to the present invention a protein comprising SEQ ID NO:1 is used in inducing or accelerating cicatrisation in the eye of a subject and/or in preventing infection in the eye of a subject.

Preferably the ocular disease is selected from the group consisting of diabetic keratinopathy, keratitis, conjunctivitis, keratoconjunctivitis, uveitis, corneal trauma, corneal abrasion, corneal burns, corneal chronic ulcer, corneal dystrophies, persistent corneal epithelial defect (PED), corneal epithelial defect after laser surgeries, corneal epithelial defect post-PRK, corneal epithelial defect post-transcorneal transplant.

SEQ ID NO:1 corresponds to the 81 amino acid mature form of SLURP-1.

In an alternative embodiment, according to the present invention a composition comprising a protein comprising SEQ ID NO:1 is used in inducing or accelerating cicatrisation, and/or in preventing infection in the eye of a subject.

The composition preferably comprises at least one biocompatible polymer.

More preferably, the biocompatible polymer is selected from the group consisting of hyaluronic acid, sugar polymers, lecithin gels, polyalanine derivates, pluronics, poly(ethylene)glycol, poloxamers, chitosan, xyloglucan, collagen, fibrin, polyorthoesters and mixtures thereof.

Even more preferably the biocompatible polymer is hyaluronic acid.

Alternatively, the biocompatible polymer is preferably a sugar polymer, even more preferably dextran (a glucose polymer).

Preferably, the dextran is a carboxymethyl dextran sulphate polymer, more preferably a ReGeneraTing Agent (RGTA®), even more preferably OTR4120 (formula I) which is marketed under the name of Cacicol 20®.

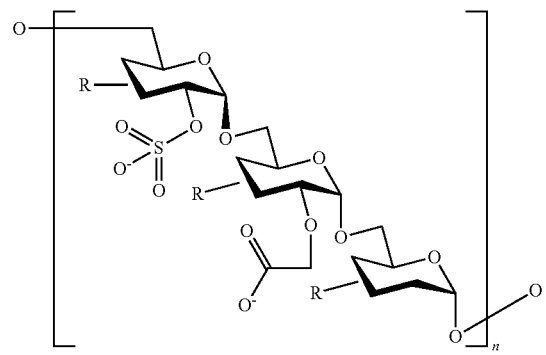

Formula I represents an analogue subunit of heparan sulfate with a glucose subunit based backbone.

The composition can be solid, semi-solid, gel-like or liquid; moreover, it can be a solution, a suspension, an emulsion or a thermosetting gel.

In an alternative embodiment the composition comprises at least one nanoparticle carrier.

The nanoparticle carrier is preferably selected from the group consisting of poly-ε-caprolactone, polycyanocrylate and chitosan.

In an alternative embodiment, the composition is in the form of an injectable viscous polymer composition. In particular the polymers of the composition are polyorthoesters.

The composition is preferably administered by topical treatment or subconjunctival injection.

More preferably, the amount of protein comprising SEQ ID NO:1 is from 5 ng to 50 µg per administration unit, more preferably from 10 ng to 10 µg per administration unit.

In a preferred embodiment the composition is administered by subconjunctival injection and the amount of protein comprising SEQ ID NO:1 is from 20 ng to 90 ng per administration unit.

EXAMPLES

Example 1: Corneal Wound Healing after Topical or Sub-Conjunctival Administration FIGS. 2 and 3 report the data of a first experiment in which the cicatrizing/ocular wound healing activity of SLURP-1 was compared using two routes of administration in a des-epithelialization model in rats. The first route of administration is a common route for ocular products used for moisture maintenance of the cornea and specifically for its ease of use: instillation (topical application). This route was used with a six times/day administration frequency at days 0 and 3 after a surgical complete des-epithelialization. Following the same surgical treatment, a second set of animals was treated by a different route of administration: the sub-conjunctival route. The latter administration was practiced only once daily at days 0 and 3.

Both routes of administration have a common feature, namely the SLURP-1 applied quantities: the group receiving instillations was treated with a solution corresponding to the highest dose used in the group treated sub-conjunctively. It could be easily conceivable that products administered via the sub-conjunctival route would be available for a longer time during wound treatment as they might be slowly released by the conjunctiva tank they are stored in; conversely treatment administered topically would be quickly eliminated from the eye surface. Following this hypothesis, the dose regimen used in the sub-conjunctival treatment was in a range from the dose used topically (5 µg) and gradually decreasing to 50 ng.

As shown in FIG. 3A, both routes of administration were capable of accelerating the wound healing process.

On day 2 after total des-epithelialization, the healing rate after a sub-conjunctival injection of 50 ng SLURP-1 was significantly higher as compared to a sub-conjunctival injection of PBS ($p<0.05$) (FIG. 3B).

The unexpected discovery was concerning the sub-conjunctival route of administration in which the cicatrizing effect was more pronounced at the lowest dose (50 ng) when compared to the dose used in topical administration which in terms of quantity is much higher.

The total administered quantity was calculated in both routes of administration regimen giving similar efficacy results (that is 1 µg/mL for sub-conjunctival and 100 µg/mL for topical route). In the topical treatment, 6 administrations of 50 µL drops were performed per day on two timely separate days with a 100 µg/mL solution. Then the final quantity used in this treatment group was 6*2*5 µg=60 µg. In the sub-conjunctival treatment, a 1 µg/mL solution was injected twice (50 µL volume) thus the overall quantity given by this route was 2*0.05 µg=0.1 µg. When comparing both administered quantities leading to similar clinical efficacy, a ratio of 600 between sub-conjunctival and topical quantities is observed.

This is clearly in favour of a severely increased efficacy of the product by this specific less common route of administration for this product in order to treat ocular wound healing and other stated clinical conditions.

More in particular, the experiment involved mechanical resection of the whole corneal epithelium performed under a surgical microscope using a 70% ethanol-soaked microsponge and a 15° surgical knife. The cornea was then rinsed with 0.9% NaCl and the effect of the treatment on corneal re-epithelialization was evaluated using topical 0.5% fluorescein, at 5 time-points after des-epithelialization (D1, D2, D3, D6 and D7 corresponding respectively to T24*h*, T48*h*, T72*h*, T144*h* and T168*h*).

Six groups of 5 animals received the following treatment:
Group 1: 50 µL vehicle subconjuntival injection at D0 and D3
Group 2: 1 µg/mL (50 µL) SLURP-1 subconjuntival injection (50 ng per administration), at D0 and D3
Group 3: 10 µg/mL (50 µL) SLURP-1 subconjuntival injection (500 ng per administration) at D0 and D3
Group 4: 100 µg/mL (50 µL) SLURP-1 subconjuntival injection (5 µg per administration) at D0 and D3
Group 5: 100 µg/mL (50 µL) SLURP-1, 6 topical instillations (5 µg per administration) at D0 and D3
Group 6: No treatment At each time-point (D1, D2, D3, D6 and D7), full-face photographs were taken using cobalt blue biomicroscope light and the green fluorescent labeling of the cornea was used to determine the shape and area of the remaining ulcer (FIG. 2). The time course of the healing rate is presented on graph for each group in order to compare "control" groups (vehicle and/or control without any treatment) versus SLURP-1 treated groups (FIG. 3A). The wound healing follow up of each cornea was performed through computer-assisted measures of the wound area ($A_t$): ratio of the fluorescein-stained area to the total corneal area. For each time point, the healing rate: $(A_{t0}-A_t)/A_{t0}$ was calculated. Results are presented as mean±SEM. An ANOVA test followed by the Dunnett's multiple comparison test or the non-parametric Mann Whitney comparison test were performed using GraphPad Prism (GraphPad Software, San Diego, U.S.A.).

The model induced a limbic insufficiency leading to corneal neovascularization and slowing the healing process. Corneas that presented a strong central ulcer were excluded from the study.

As shown in FIG. 3B, on day 2 after total des-epithelialization, the healing rate after a sub-conjunctival injection of 50 ng of SLURP-1 is significantly higher as compared to a sub-conjunctival injection of PBS ($p<0.05$ Dunnett) and controls ($p<0.01$ Dunnett). The healing rate after instillation of SLURP-1 is also significantly higher than controls ($p<0.05$, Dunnett), but is not significantly different than after PBS injection.

As shown in FIG. 3C, on day 3 after total des-epithelialization, the healing rates of the SCJ 50 ng SLURP-1 treated group and instillation group are significantly higher than the control group ($p<0.05$, Dunnett) but are not significantly different than the healing rate with PBS.

This observation suggests that the SCJ procedure (or PBS) itself induces a response promoting corneal healing.

As regards neovascularization, neovessels were visible in each group just after the beginning of the re-epithelialization process. The qualitative follow up of the corneal neovascularization did not demonstrate any difference between the SLURP-1-treated groups and controls. This is a very important observation showing that the healing properties of SLURP-1 are not associated with proangiogenic effects and do not impair restoration of corneal transparency.

This means that SLURP-1 showed a significant corneal effect after sub-conjunctival administration and instillation, in the absence of side effects, and particularly, in the absence of corneal neovascularization that is associated with limbal deficiency, demonstrating that the healing effect is not linked to the corneal trans-differentiation process.

Example 2: Corneal Wound Healing after Topical or Sub-Conjunctival Administrations in a Calibrated Corneal Des-Epithelialization Model Following the preliminary results obtained in the first corneal des-epithelialization model that implied not only a healing process but also a limbic insufficiency, a calibrated model of alcohol-induced des-epithelialization was chosen as a second study model in order to focus on the corneal healing properties of SLURP-1. The objective of this study was to confirm the preliminary results showing an enhancement of the re-epithelialization by the tested protein as compared to controls, and to evaluate a possible dose-response induced by the protein.

The model involved a calibrated wound created using a trephine causing a 4 mm diameter circular incision. Healing of such a minute wound is very fast even in the absence of any treatment (sometime around 2 days). Hence administrations were performed only once, on the day of incision, and efficacy was evaluated during the first 48 h by an examination twice a day.

The injected volume was adjusted from the first experiment; doses were equivalent with twice the administration volume and half concentrated solutions. This different dosing was chosen to increase the retention time in the tank created by sub-conjunctival injection leading to a prolonged presence of SLURP-1 on the corneal surface to compensate the unique administration performed in this standardized model.

In this second experimental model, SLURP-1 effects were confirmed; namely the sub-conjunctival route with low injected quantities was 6 to 60 times more efficient in accelerating ocular wound healing when compared to the topical route.

More in particular, corneal epithelial wounds were obtained as described by Hattori et al [25]. Briefly, after systemic and topical anesthesia, a trephine was used to make a 4-mm-diameter circular incision that was centered on the cornea. Then, the 4-mm diameter circular filter paper, which had been soaked with 70% ethanol, was placed on the incised area for 5 seconds. After a gentle wash with 5 mL saline, the detached corneal epithelium was removed.

Treatment was administered only in the right eye via 1 single subconjunctival injection or 6 instillations at D0 (time of corneal des-epithelialization). Five groups of 4-6 animals received the following treatment:

Group 1: 0.5 µg/mL (100 µL) SLURP-1 sub-conjunctival injection (50 ng per administration), at D0

Group 2: 5 µg/mL (100 µL) SLURP-1 sub-conjunctival injection (500 ng per administration), at D0

Group 3: 50 µg/mL (100 µL) SLURP-1 sub-conjunctival injection (5 µg per administration), at D0

Group 4: 100 µg/mL (50 µL) SLURP-1 (5 µg per administration), 6 instillations at D0

Group 5: Vehicle subconjuntival injection (100 µL) at D0

Figure 4:
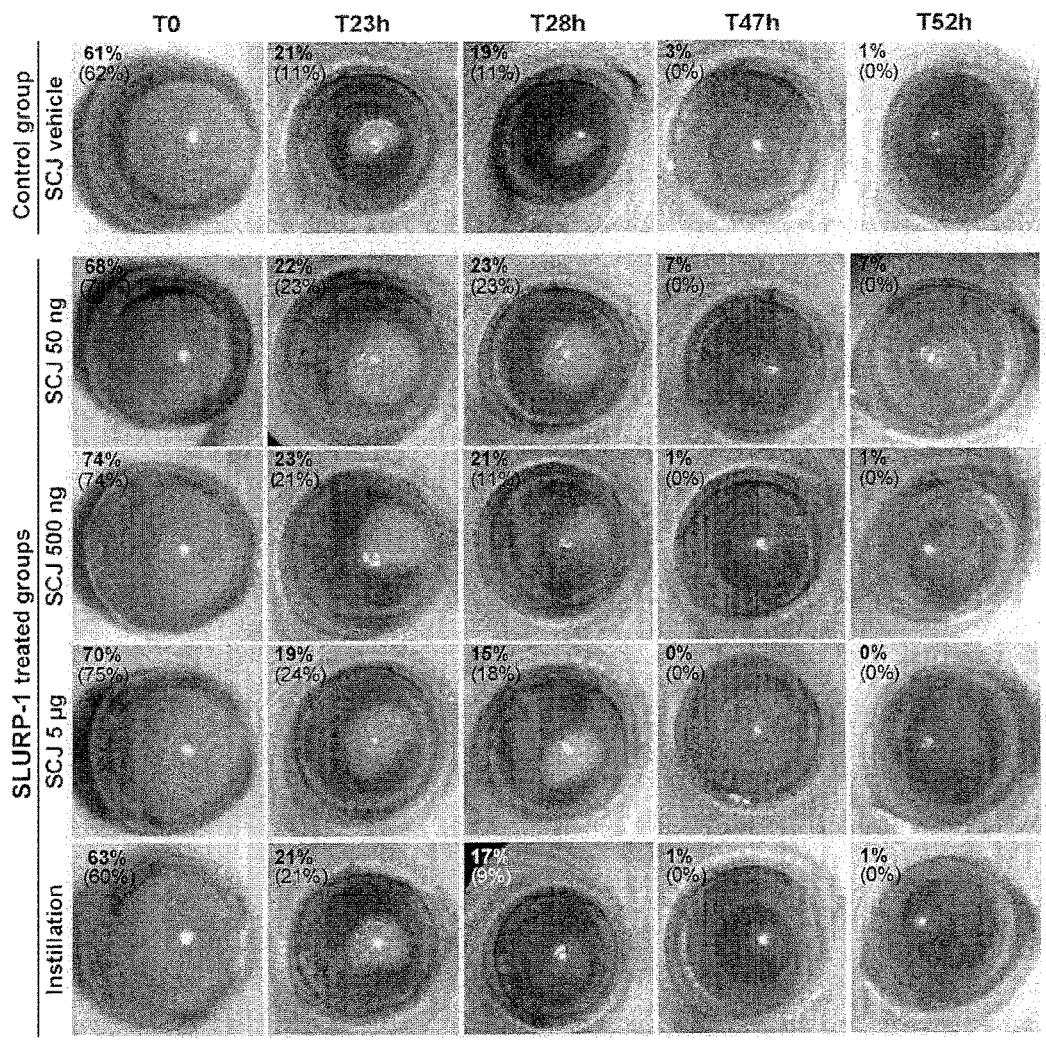
FIG. 4 shows images of fluorescein staining of corneal epithelial wounds at the indicated time points after calibrated alcohol-induced des-epithelialization in PBS and SLURP-1 treated groups. Bold percentages indicate the group mean of the corneal wound surface, and percentages in brackets indicate the value of the representative cornea for the considered group.

The right corneas were examined with a biomicroscope. Each right cornea received one drop of 0.5% fluorescein (Novartis pharma S.A.S) and was examined using a cobalt blue light. Digital photographs were taken through the binocular. During the healing follow-up in the calibrated corneal des-epithelialization models, corneas were examined at day 0, day 1 AM (T$23h$), day 1 PM (T$28h$), day 2 AM (T$47h$) and day 2 PM (T$56h$) (FIG. 4).

Digital photographs were analyzed with imaging software (Adobe Photoshop). For each eye and each time-point, the area of the remaining ulcer was compared to the total corneal area. Time course of the healing rate is presented on graph for each group in order to compare control (vehicle and/or control without any treatment) versus SLURP-1 treated groups. Results are presented as mean±SEM. An ANOVA test followed by the Dunnett's multiple comparison test or the non-parametric Mann Whitney comparison test were performed using GraphPad Prism (GraphPad Software, San Diego, U.S.A.).

Figure 5A:
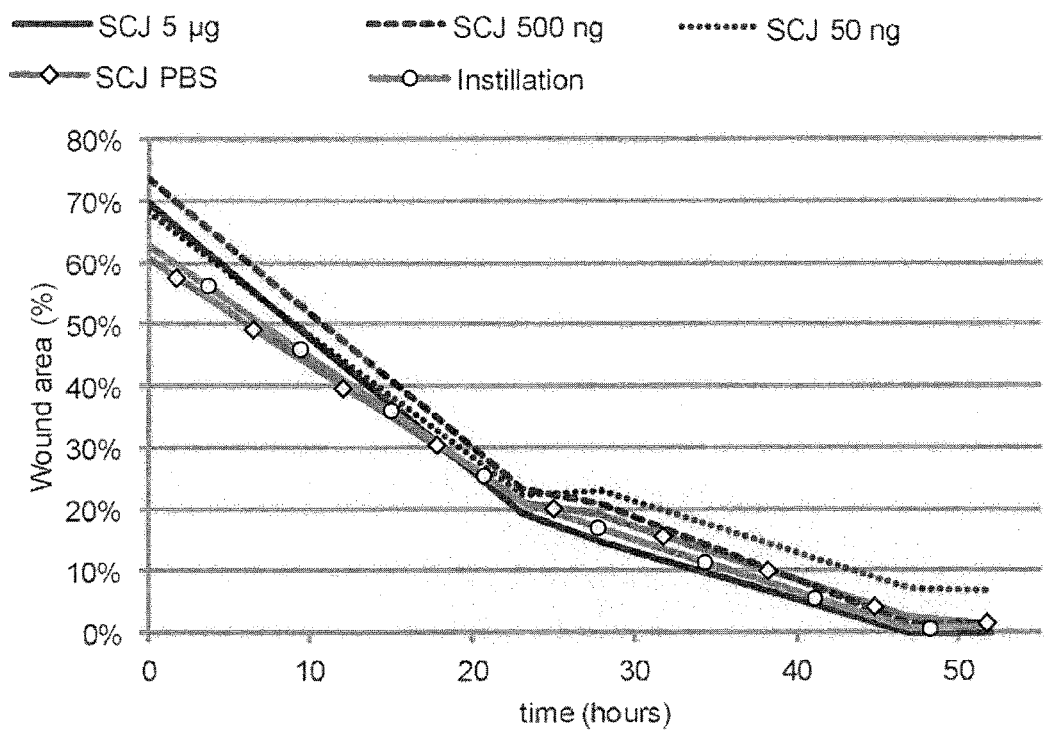
FIG. 5A is a graph showing the time course of measured wound area from day 0 to day 2 after des-epithelialization in control and SLURP-1 treated groups.
Figure 5B:
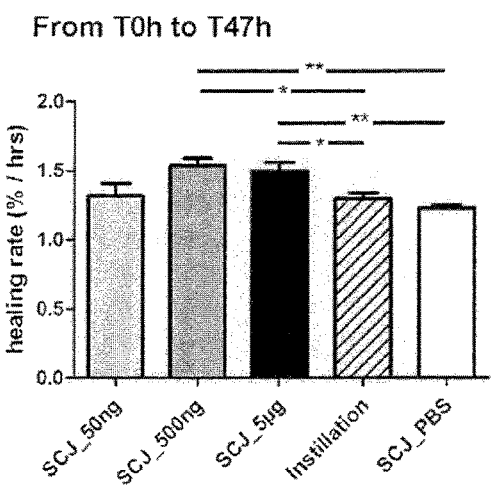
FIG. 5B is a graph of the calculated healing rate between T0$h$ and T47$h$ after calibrated des-epithelialization in control and SLURP-1 treated groups.
Figure 5C:
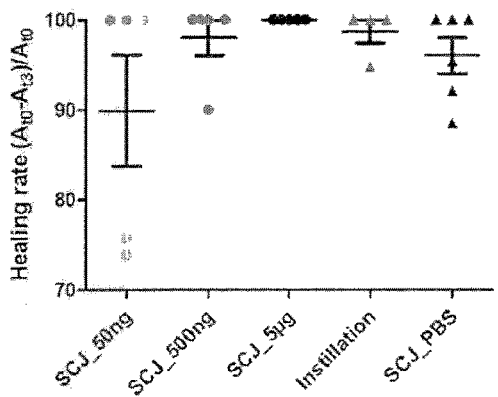
FIG. 5C is a graph of the degree of wound healing at T47$h$ after calibrated des-epithelialization. The degree of wound healing was calculated by the ratio: area of the fluorescein wound at T47$h$/area of the fluorescein wound at baseline, for each cornea, for each group, and expressed in percentage.

The time courses of the corneal wound closure in the control and SLURP-1 treated groups are shown in FIG. 5A. When comparing the healing rate calculated between T$0h$ and T$47h$, SCJ injection of 500 ng and 5 µg of SLURP-1 significantly increased the healing rate as compared to the instillation or PBS sub-conjunctival administration groups (FIG. 5B). There was a dose response effect since no significant effect was observed in the 50 ng-SCJ injection group. Moreover, at T$47h$, the number of totally healed corneas was higher in the groups treated with sub-conjunctival injection of SLURP-1 at either 500 ng or 5 µg (FIG. 5C), with a noticed difference between the 500 ng (4 out of 5 corneas) and 5 µg (5 out of 5 corneas) as compared to the control group (3 out of 6 corneas).

Example 3: Wound Closure Assay with SLURP-1 on Human Corneal Epithelial Cell Line hTCEpi A wound closure assay used to monitor cell migration is the Oris Cell Migration Assay-Collagen I Coated from Platypus Technologies. Cell seeding density was determined visually using an inverted microscope. 100 microliter of optimal cell seeding density was pipetted into test wells and incubated in a humidified chamber (37° C., 5% $CO_2$) for 1-4 hours to allow cell attachment. Cytochalasin D was used as positive control.

Figure 6:
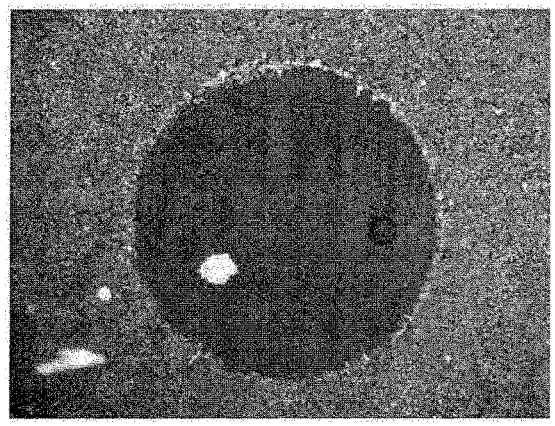
FIG. 6 shows photographs of wound healing experiments carried out by treating the human corneal epithelial cell line hTCEpi with SLURP-1.
Figure 6:
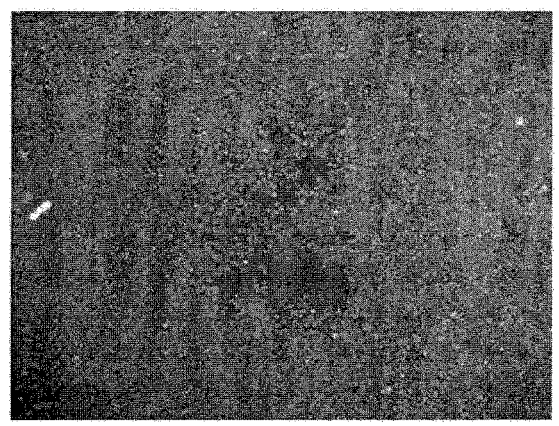
Figure 6:
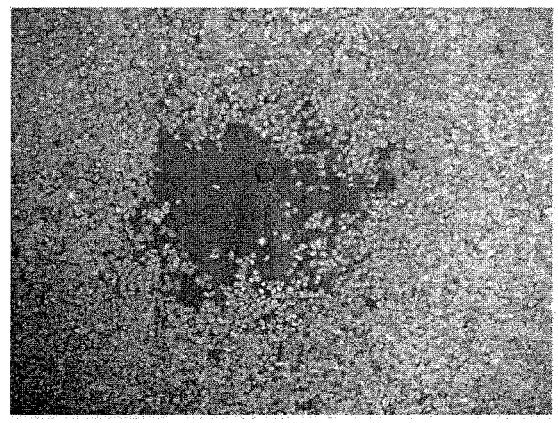

Experiments were carried out in triplicate with increasing amounts of SLURP-1. The amounts tested were 0 µg/ml (negative control), 1 µg/ml, 5 µg/ml, 10 µg/ml, 15 µg/ml, 25 µg/ml and 50 µg/ml. After 24 h the wounded areas on the plate were healed at different degrees. Cells treated with 10 µg/ml of SLURP-1 showed optimal wound healing as may be seen in FIG. 6.

From an analysis of the above data the advantages the present invention allows to achieve are apparent.

In particular, an effective association between a specific concentration of SLURP-1 and a particular route of administration gives optimal results in terms of accelerated healing rate and faster reduced wound area, in particular protecting ocular surface from infection.

Moreover, the healing properties of SLURP-1 are not associated with proangiogenic effects and do not impair restoration of corneal transparency.

REFERENCES

1. Ploug, M. and V. Ellis, Structure-function relationships in the receptor for urokinase-type plasminogen activator.

1. Comparison to other members of the Ly-6 family and snake venom alpha-neurotoxins. FEBS Lett, 1994. 349(2): p. 163-8.
2. Ploug, M., et al., Localization of the disulfide bonds in the NH2-terminal domain of the cellular receptor for human urokinase-type plasminogen activator. A domain structure belonging to a novel superfamily of glycolipid-anchored membrane proteins. J Biol Chem, 1993. 268(23): p. 17539-46.
3. Casey, J. R., et al., The structure of the urokinase-type plasminogen activator receptor gene. Blood, 1994. 84(4): p. 1151-6.
4. Adermann, K., et al., Structural and phylogenetic characterization of human SLURP-1, the first secreted mammalian member of the Ly-6/uPAR protein superfamily. Protein Sci, 1999. 8(4): p. 810-9.
5. Tsuji, H., et al., SLURP-2, a novel member of the human Ly-6 superfamily that is up-regulated in psoriasis vulgaris. Genomics, 2003. 81(1): p. 26-33.
6. Ward, K. M., et al., Identification of recurrent mutations in the ARS (component B) gene encoding SLURP-1 in two families with mal de Meleda. J Invest Dermatol, 2003. 120(1): p. 96-8.
7. Eckl, K. M., et al., Mal de Meleda (MDM) caused by mutations in the gene for SLURP-1 in patients from Germany, Turkey, Palestine, and the United Arab Emirates. Hum Genet, 2003. 112(1): p. 50-6.
8. Fischer, J., et al., Mutations in the gene encoding SLURP-1 in Mal de Meleda. Hum Mol Genet, 2001. 10(8): p. 875-80.
9. Fischer, J., et al., Genetic linkage of Meleda disease to chromosome 8qter. Eur J Hum Genet, 1998. 6(6): p. 542-7.
10. Tone, M., L. A. Walsh, and H. Waldmann, Gene structure of human CD59 and demonstration that discrete mRNAs are generated by alternative polyadenylation. J Mol Biol, 1992. 227(3): p. 971-6.
11. Reiter, R. E., et al., Prostate stem cell antigen: a cell surface marker overexpressed in prostate cancer. Proc Natl Acad Sci USA, 1998. 95(4): p. 1735-40.
12. Horie, M., et al., Isolation and characterization of a new member of the human Ly6 gene family (LY6H). Genomics, 1998. 53(3): p. 365-8.
13. Shan, X., et al., Characterization and mapping to human chromosome 8q24.3 of Ly-6-related gene 9804 encoding an apparent homologue of mouse TSA-1. J Immunol, 1998. 160(1): p. 197-208.
14. Brakenhoff, R. H., et al., The human E48 antigen, highly homologous to the murine Ly-6 antigen ThB, is a GPI-anchored molecule apparently involved in keratinocyte cell-cell adhesion. J Cell Biol, 1995. 129(6): p. 1677-89.
15. Mao, M., et al., RIG-E, a human homolog of the murine Ly-6 family, is induced by retinoic acid during the differentiation of acute promyelocytic leukemia cell. Proc Natl Acad Sci USA, 1996. 93(12): p. 5910-4.
16. Samson, A. O. and M. Levitt, Inhibition mechanism of the acetylcholine receptor by alpha-neurotoxins as revealed by normal-mode dynamics. Biochemistry, 2008. 47(13): p. 4065-70.
17. Samson, A., et al., The mechanism for acetylcholine receptor inhibition by alpha-neurotoxins and species-specific resistance to alpha-bungarotoxin revealed by NMR. Neuron, 2002. 35(2): p. 319-32.
18. Chimienti, F., et al., Identification of SLURP-1 as an epidermal neuromodulator explains the clinical phenotype of Mal de Meleda. Hum Mol Genet, 2003. 12(22): p. 3017-24.
19. Mastrangeli, R., et al., ARS Component B: structural characterization, tissue expression and regulation of the gene and protein (SLURP-1) associated with Mal de Meleda. Eur J Dermatol, 2003. 13(6): p. 560-70.
20. Chernyaysky, A. I., et al., Coupling of ionic events to protein kinase signaling cascades upon activation of alpha7 nicotinic receptor: cooperative regulation of alpha2-integrin expression and Rho kinase activity. J Biol Chem, 2009. 284(33): p. 22140-8.
21. Arredondo, J., et al., Biological effects of SLURP-1 on human keratinocytes. J Invest Dermatol, 2005. 125(6): p. 1236-41.
22. Grando, S. A., M. R. Pittelkow, and K. U. Schallreuter, Adrenergic and cholinergic control in the biology of epidermis: physiological and clinical significance. J Invest Dermatol, 2006. 126(9): p. 1948-65.
23. Grando, S. A., Cholinergic control of epidermal cohesion. Exp Dermatol, 2006. 15(4): p. 265-82.
24. Favre, B., et al., SLURP1 is a late marker of epidermal differentiation and is absent in Mal de Meleda. J Invest Dermatol, 2007. 127(2): p. 301-8.
25. Hattori, M., et al., Effects of all-trans retinoic acid nanoparticles on corneal epithelial wound healing. Graefes Arch Clin Exp Ophthalmol, 2011.
26. Chernyaysky, A. I., et al., Novel cholinergic peptides SLURP-1 and -2 regulate epithelialization of cutaneous and oral wounds. Wound Rep Reg, 2012. 20: p. 103-113.

The invention claimed is:

1. A method for promoting closure of a corneal wound in an eye of a subject in need thereof, comprising administering to the eye of the subject having the corneal wound in need of closure a composition that comprises (i) a SLURP-1 protein comprising the amino acid sequence set forth in SEQ ID NO:1, in an amount sufficient to promote a rate of corneal wound closure that is accelerated relative to the rate of healing when the SLURP-1 protein is not administered, and (ii) at least one biocompatible polymer that comprises either or both of hyaluronic acid and a sugar polymer which comprises a carboxymethyl dextran sulphate polymer.

2. The method of claim 1, wherein the biocompatible polymer further comprises a polymer selected from the group consisting of lecithin gels, polyalanine derivatives, pluronics, poly(ethylene)glycol, poloxamers, chitosan, xyloglucan, collagen, fibrin, polyorthoesters and mixtures thereof.

3. The method of claim 1, wherein the carboxymethyl dextran is:

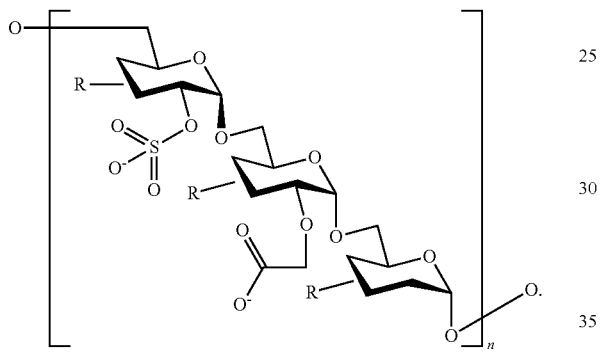

4. A method for promoting closure of a corneal wound in an eye of a subject in need thereof, comprising administering to the eye of the subject having the corneal wound in need of closure a composition that comprises (i) a SLURP-1 protein comprising the amino acid sequence set forth in SEQ ID NO:1 in an amount sufficient to promote a rate of corneal wound closure that is accelerated relative to the rate of corneal wound closure when the SLURP-1 protein is not administered, and (ii) at least one nanoparticle carrier.

5. The method of claim 4, wherein the nanoparticle carrier is selected from the group consisting of poly-ε-caprolactone, polycyanocrylate and chitosan.

6. The method of claim 4, wherein the composition is administered by topical treatment or subconjunctival injection.

7. The method of claim 6, wherein at least one of:
(a) the composition that is administered comprises from 5 ng to 50 µg of the SLURP-1 protein,
(b) the composition that is administered comprises from 10 ng to 10 µg of the SLURP-1 protein,
(c) the composition that is administered comprises from 20 ng to 90 ng of the SLURP-1 protein and the composition is administered by subconjunctival injection, or
(d) the composition that is administered comprises from 40 ng to 60 ng of the SLURP-1 protein and the composition is administered by subconjunctival injection.

8. The method of claim 1 wherein the composition is administered by topical treatment or subconjunctival injection.

9. The method of claim 8 wherein at least one of:
(a) the composition that is administered comprises from 5 ng to 50 µg of the SLURP-1 protein,
(b) the composition that is administered comprises from 10 ng to 10 µg of the SLURP-1 protein,
(c) the composition that is administered comprises from 20 ng to 90 ng of the SLURP-1 protein and the composition is administered by subconjunctival injection, or
(d) the composition that is administered comprises from 40 ng to 60 ng of the SLURP-1 protein and the composition is administered by subconjunctival injection.

10. A method for promoting closure of a corneal wound in an eye of a subject in need thereof, comprising administering to the eye of the subject having the corneal wound in need of closure a composition that comprises a SLURP-1 protein comprising the amino acid sequence set forth in SEQ ID NO:1, in an amount sufficient to promote a rate of corneal wound closure that is accelerated relative to the rate of healing when the SLURP-1 protein is not administered.

11. The method of claim 10, wherein the composition is administered by topical treatment or subconjunctival injection.

12. The method of claim 11 wherein at least one of:
(a) the composition that is administered comprises from 5 ng to 50 µg of the SLURP-1 protein,
(b) the composition that is administered comprises from 10 ng to 10 µg of the SLURP-1 protein,
(c) the composition that is administered comprises from 20 ng to 90 ng of the SLURP-1 protein and the composition is administered by subconjunctival injection, or
(d) the composition that is administered comprises from 40 ng to 60 ng of the SLURP-1 protein and the composition is administered by subconjunctival injection.

13. The method of claim 10, wherein administering to the eye comprises sub-conjunctivally injecting the composition.

14. The method of claim 10, wherein the composition is administered by topical treatment or subconjunctival injection and wherein at least one of:
(a) the composition that is administered comprises from 5 ng to 50 µg of the SLURP-1 protein,
(b) the composition that is administered comprises from 10 ng to 10 µg of the SLURP-1 protein,
(c) the composition that is administered comprises from 20 ng to 90 ng of the SLURP-1 protein and the composition is administered by subconjunctival injection, or
(d) the composition that is administered comprises from 40 ng to 60 ng of the SLURP-1 protein and the composition is administered by subconjunctival injection.

* * * * *